United States Patent [19]

Relenyi et al.

[11] Patent Number: 4,613,671

[45] Date of Patent: Sep. 23, 1986

[54] PROCESS FOR THE PREPARATION OF MELDRUM'S ACID

[75] Inventors: Attila G. Relenyi; David E. Wallick, both of Midland, Mich.; Jill D. Streit, Columbus, Ind.

[73] Assignee: The Dow Chemical Company, Midland, Mich.

[21] Appl. No.: 749,145

[22] Filed: Jun. 26, 1985

[51] Int. Cl.[4] .......................................... C07D 319/06
[52] U.S. Cl. ................................................... 549/274
[58] Field of Search ........................................ 549/274

[56] References Cited

U.S. PATENT DOCUMENTS 4,065,440 12/1977 Serres, Jr. .................. 260/75 R
4,496,368 1/1985 Kaufman et al. .................. 44/63

OTHER PUBLICATIONS

Meldrum, J. Chem. Soc., 93, pp. 598–601 (1908).
Ott, Annalen, 401, pp. 159–177 (1913).
Michael et al., J. Amer. Chem. Soc., vol. 55, pp. 3684–3695 (1933).
Davidson et al., J. Amer. Chem. Soc., vol. 70, pp. 3426–3428 (1948).
McNab, Chem. Soc. Rev., 1(3), pp. 345–358 (1978).

*Primary Examiner*—Dolph H. Torrence
*Attorney, Agent, or Firm*—Thomas R. Savitsky

[57] ABSTRACT

A process for producing Meldrum's acid in excellent yield wherein acetic anhydride is added in a slow, controlled manner to a mixture of acetone, malonic acid and an acid catalyst.

15 Claims, No Drawings

PROCESS FOR THE PREPARATION OF MELDRUM'S ACID

BACKGROUND OF THE INVENTION

The preparation of Meldrum's acid (originally described as a β-lactonic acid from acetone and malonic acid, also known as diisopropylidene methylene dimalonate; 2,2-dimethyl-1,3-dioxane-4,6-dione; or malonic acid cyclic isopropylidene ester) was first reported by Meldrum in 1908 (see Meldrum, A.N., J. Chem. Soc. 93, 598-601 (1908)). Meldrum's acid is useful as an intermediate for preparing a wide variety of products (see McNab, H., Chem. Soc. Rev. 7 (3), 345-358 (1978)). A specific example of where Meldrum's acid has been shown to be useful can be found in U.S. Pat. No. 4,065,440 in which Meldrum's acid is shown to be useful in a process for increasing the molecular weight of polyesters.

Known methods for preparing Meldrum's acid result in poor yields, typically less than 50 percent (see, for example, U.S. Pat. No. 4,065,440, Example I). A process giving a poor yield of Meldrum's acid is, for many purposes, economically unacceptable.

The present invention is directed to a process which provides significantly improved yields of Meldrum's acid as compared to processes taught in the prior art.

SUMMARY OF THE INVENTION

The present invention concerns a process for preparing Meldrum's acid in excellent yield. More specifically the process of the present invention comprises the steps of:

(a) mixing acetone, malonic acid, and an acid catalyst in molar ratios from about 1.0:1.0:0.005 to about 2.3:1.0:0.12, respectively, to form a mixture comprising: a solution phase of the acetone, acid catalyst, and from about 5 to about 25 mole percent of the malonic acid; and a solid phase of from about 75 to about 95 mole percent of the malonic acid, (b) adding acetic anhydride to the mixture obtained from step (a), the total amount of acetic anhydride which is added is from about 0 percent molar excess to about 150 percent molar excess relative to the total malonic acid molar concentration, said addition of acetic anhydride occurring at a rate such that at any given time during the addition of acetic anhydride the concentration of unreacted acetic anhydride in the mixture does not exceed about 14 mole percent relative to the malonic acid molar concentration concurrently present in the solution phase.

DETAILED DESCRIPTION OF THE INVENTION

It is critical for the process of the present invention that the concentration of unreacted acetic anhydride during the addition of acetic anhydride not exceed about 14 mole percent relative to the malonic acid molar concentration concurrently present in the solution phase. Typically this is achieved by controlled addition, for example, slow dropwise or shotwise addition, of acetic anhydride to the mixture obtained from step (a) of the process. An analytical method based on nuclear magnetic resonance (NMR), gas chromatography (GC), or high performance liquid chromatography (HPLC) can be used to monitor solution concentrations of malonic acid, acetic anhydride and acetone during a particular run to establish the exact addition rate of acetic anhydride. The rate of addition of acetic anhydride will vary according to the exact proportions of reactants, temperature, volume, and other process conditions. However, for applications wherein the desired yield of Meldrum's acid is between about 1 and 7 pounds, the rate of addition of acetic anhydride will typically vary between about 0.25 milliliters (ml) per minute and 20 ml per minute, with a preferred rate being less than about 2 ml per minute. Scale up runs have to be methodically followed to ensure optimum processing conditions to achieve satisfactory results.

Although a satisfactory yield of Meldrum's acid will be obtained when the concencentration of unreacted acetic anhydride during addition of acetic anhydride does not exceed about 14 mole percent, generally it is preferred to keep the concentration of unreacted acetic anhydride during said addition at 0.1 mole percent or less, said percentages being based on the malonic acid molar concentration concurrently present in the solution phase. The most critical time for the addition of acetic anhydride is during the initial time of addition. As used herein, the phrase "initial time of addition" refers to that time during which not more than 25 percent of the total acetic anhydride is added to the reaction mixture. Therefore, it is particularly preferred to keep the concentration of unreacted excess acetic anhydride during the initial time of addition at 0.1 mole percent or less relative to the malonic acid molar concentration concurrently present in the solution phase.

For step (a), the malonic acid, acetone and acid catalyst can be mixed together in any order; however, the preferred order of addition is acetone first, malonic acid second, and the acid catalyst third. Addition of acid catalyst last minimizes the possibility of any undesired side reaction between acetone and the acid catalyst.

For the process of the present invention to proceed satisfactorily, the temperature can vary considerably, however, the temperature is typically maintained between about −15° and 25° C.; a preferred temperature is about 0° C.

A preferred molar ratio of acetone, malonic acid and acid catalyst is about 1.14:1.0:0.06, respectively.

Another preferred embodiment of the present invention is to carry out the process of the invention in the absence of oxygen or with minimal exposure to oxygen. This typically can be accomplished by purging or blanketing the reaction mixture with an inert gas, for example, nitrogen.

The acetone, malonic acid, and acid catalyst in step (a) are mixed (e.g., stirred) which forms a slurry. The slurry is allowed to stand for a period of time not greater than about 8 hours, with the preferred time being not greater than about 2 hours. Generally, the longer the reactants of step (a) are allowed to stand together, the greater the probability of discoloration due to the presence of color bodies. Such discoloration may be undesired where the Meldrum's acid is to be used in applications wherein color is an important characteristic. Color bodies have not altered the purity assay of Meldrum's acid and do not appear to be more than about one percent of the total composition of isolated Meldrum's acid.

Although the total amount of acetic anhydride used in the process of the present invention can be in the range of from about 0 percent molar excess to about 150 percent molar excess, it is preferred to have about 25 percent molar excess, said percent molar excesses being relative to the total molar amount of malonic acid. An excess of acetic anhydride is typically required in order to compensate for any side reactions such as the reaction of acetic anhydride with adventitious moisture to form acetic acid.

Typically the total reaction time for step (b) can take up to about 3 days or longer depending upon the other reaction conditions. However, a preferred reaction time is about 15 to about 18 hours when the temperature is about 0° C. Typically the reaction is terminated when substantially the molar equivalent of acetone relative to the total malonic acid concentration is reacted.

As the process of the present invention proceeds and acetic anhydride is being added, Meldrum's acid is being formed and malonic acid is being consumed; presumably the malonic acid is being consumed from the solution phase. It is further presumed that as malonic acid in the solution phase is reacting to form Meldrum's acid, more malonic acid will convert from the solid phase to the solution phase (i.e., dissolve). Therefore, until the latter part of the reaction period, the concentration of malonic acid in the solution phase (and presumably available for reacting to form Meldrum's acid) will remain relatively constant while the amount of malonic acid in the solid phase becomes depleted. However, the exact concentrations of all reactants and products at any given time will depend upon the complex relationships among all compounds present (e.g., equilibria, solubilities, and the like). As is readily apparent, in order not to exceed the desired concentration of unreacted acetic anhydride, the reaction is usually terminated with a trace amount of free malonic acid remaining; however, this is insignificant since an excellent yield of Meldrum's acid is already produced.

Acid catalysts suitable for use in the process of the present invention include strong mineral acids such as hydrochloric acid, nitric acid, sulfuric acid, and the like, and further include Lewis acids such as aluminum trichloride, and the like. A preferred acid catalyst is sulfuric acid.

The process of the present invention typically yields greater than about 75 percent of the theoretical maximum yield of Meldrum's acid, and more typically yields greater than about 90 percent of the theoretical maximum yield of Meldrum's acid.

It is not desired to be bound by any particular mechanism or theory, but it is believed that the process of the present invention can be better understood in view of the following probable reaction scheme:

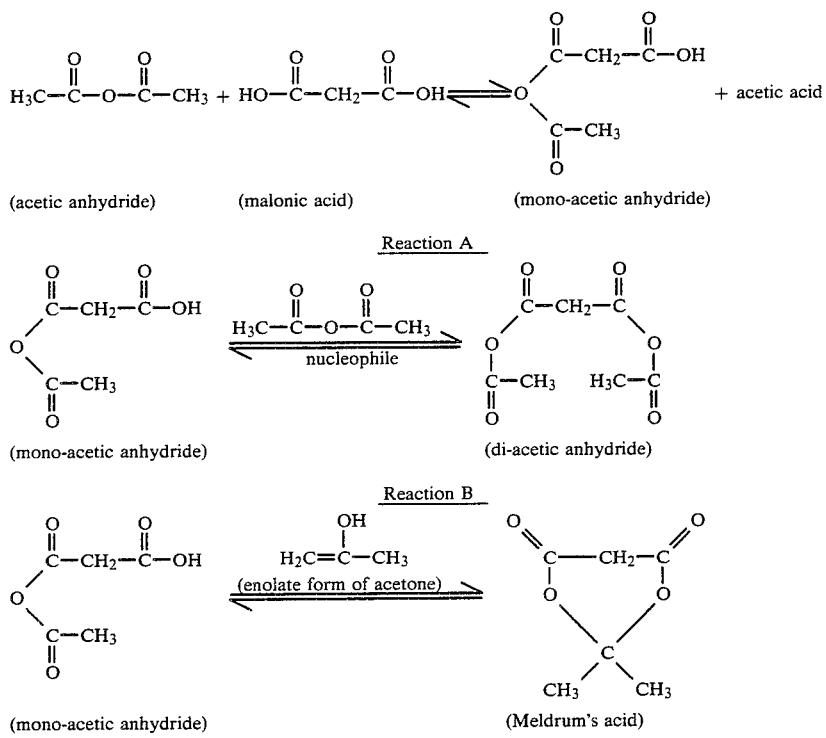

As can be seen, one equivalent of acetic anhydride reacts with one equivalent of malonic acid to form an intermediate which is a mono-acetic anhydride of malonic acid. Once this intermediate is formed, two alternative primary reactions can occur as follows:

Reaction A

The mono-acetic anhydride intermediate reacts with another equivalent of acetic anhydride to form a di-acetic anhydride.

Reaction B

The mono-acetic anhydride intermediate reacts with the enolate form of acetone (enolate is produced by the reaction of acetone with an acid catalyst) to form Meldrum's acid.

It is clear that in improving the yield of Meldrum's acid, Reaction A is undesired and is non-productive, whereas Reaction B results in formation of Meldrum's acid and is therefore desired. The process of the present invention minimizes Reaction A and maximizes Reaction B so that an excellent yield of Meldrum's acid is obtained. It should be noted that the di-acetic anhydride can convert back into the mono-acetic anhydride in the presence of a nucleophile such as water.

The process of the present invention maximizes Reaction B by providing a sufficient quantity of acid catalyst so that the concentration of the enolate form of acetone will be optimal. The process of the present invention further provides for a slow, controlled addition of acetic anhydride to a system comprising malonic acid, acetone, and an acid catalyst so that after formation of the mono-acetic anhydride intermediate, said intermediate rapidly reacts with the enolate form of acetone to form Meldrum's acid before said intermediate can react with another equivalent of acetic anhydride to form the undesired di-acetic anhydride.

Other than Meldrum's acid, the only significant product produced by the process of the present invention is acetic acid. Therefore, a convenient procedure to control the rate of addition of acetic anhydride is to monitor the level of acetic acid produced in the reaction mixture. A convenient way to optimize runs is to keep the moles of acetic acid being formed about equal to the moles of malonic acid being consumed; however, side reactions of acetic anhydride with adventitious moisture must be considered.

The present invention is further illustrated by the following examples; however, these examples should not be interpreted as a limitation upon the scope of the present invention.

EXAMPLE 1

ANALYTICAL METHODS

HPLC Method For Meldrum's Acid

To obtain HPLC data, samples were chromatographed on a reverse-phase Partisil 10/25 ODS-2 column (Whatman, Inc., 9 Bridewell Place, Clifton, NJ 07014) under the following conditions: eluent, 95:5 water/acetonitrile containing 10 milliliters (ml) of 1 molar (M) sulfuric acid per liter; flow rate, 1.5 to 2.0 ml/minute; ultraviolet detector, Kratos Spectroflow 757 (Kratos Analytical, 170 Williams Dr., Ramsey, NJ 07446) at 214 nanometers (nm), 0.01 absorbance units full scale. This method was used only to assay Meldrum's acid in the samples, as interferences occured for other desired analytes. For reaction samples, assays were obtained on 1% weight/volume (w/v) solutions of reaction liquor samples in acetonitrile. When testing the purity of the products, assays were obtained from 0.2% w/v solutions of product in acetontrile. An external standard of 0.202% w/v Meldrum's acid (recrystallized from methyl-t-butyl ether) in acetonitrile was used. Elemental analyses for carbon and hydrogen were performed to indicate the standard's purity (Meldrum's acid).

Spectroscopic Method

Nuclear magnetic resonance spectra were obtained on a Varian EM360L NMR Spectrometer (Varian Associates, 611 Hansen Way, Palo Alto, CA 94303). Reaction liquor samples were dissolved in deuterated acetonitrile, using tetramethylsilane (TMS) as the zero reference and p-dibromobenzene as an internal standard. Chemical shifts observed are as follows:

| Compound | Proton Type | Chemical Shift |
| --- | --- | --- |
| acetic acid | methyl | 2.02 parts per million (ppm) |
| acetone | methyl | 2.10 ppm |
| acetic anhydride | methyl | 2.18 ppm |
| malonic acid | methylene | 3.35 ppm |
| Meldrum's acid | methyl | 1.73 ppm |
|  | methylene | 3.67 ppm |

-continued

| Compound | Proton Type | Chemical Shift |
| --- | --- | --- |
| p-dibromobenzene | aromatic | 7.43 ppm |

Chemical shifts of the hydroxyl protons of acetic acid and malonic acid varied on different spectra, and thus were not monitored.

Preparation of Standard for NMR

A standard that would produce a singlet in the aromatic region was desired in order to avoid interference with the reaction components. p-Dibromobenzene was found to be soluble in deuterated acetonitrile, the solvent being used for reaction samples, and to give a desired downfield singlet (4 H). A solution of 9.69% w/v p-dibromobenzene (purified by sublimation) in $CD_3CN$ (with TMS) was made. Scans of this solution showed that this concentration gives measurable peak heights in the amplitude range at which reaction samples are generally run.

NMR Internal Standard Method

A known weight of reaction liquor is placed in an NMR tube with a known weight of standard solvent (9.69% w/w p-dibromobenzene in acetonitrile/TMS). The NMR scan of the solution is made, the peaks are integrated, and the peak heights are measured. To determine the concentration of each reaction component, the following method is used:

Grams (g) solvent added x (0.0969g p-$Br_2$benzene/1 g solvent) x (1 mole p-$Br_2$benzene/235.91g) x ($10^3$ mmole $Br_2$benzene/

1 mole p-$Br_2$benzene) x (4 mmole H/mmole $Br_2$benzene) x (1/height (ht.) of p-$Br_2$benzene peak) = mmole H/centimeter (cm)

This calculation gives the number of mmole of hydrogen per centimeter of integration height. This value is then used to calculate the mmole and the weight of each reaction component as follows (using acetone as the example):

mmole of acetone = (mmole H/cm) × ht. of acetone peak × (1 mmole acetone/6 mmole H)

weight (wt.) of acetone = mmole acetone (from above) × (1 mole acetone/1000 mmole acetone) × (58.08g acetone/mole acetone)

These calculations are done for each reaction component, substituting the appropriate number of hydrogens and molecular weight. The total mmole of the reaction sample is then calculated by adding together the mmole of each component, and the total weight of the liquor sample by NMR is found by adding together all of the individual weights of the reaction components. The percent difference between the weight found by NMR and the actual weight is calculated. The weight percent and mole percent of each component is found as follows (using acetone as an example):

wt. % acetone = (NMR wt. acetone/NMR wt. sample) × 100 mole % acetone = (NMR mmole acetone/NMR mmole sample) × 100

EXAMPLE 2

Preparation of Meldrum's Acid

Malonic acid (104.06 grams (g), 1.00 mole), acetone (85 ml, 1.14 mole), and sulfuric acid (3.0 ml, 0.06 mole) were placed in a reactor at 0° C. with stirring under nitrogen purge. Within one half hour, addition of acetic anhydride (120 ml, 1.25 mole) was begun dropwise at a rate of approximately 2 ml/min. The mixture began as a white slurry and gradually turned pale yellow by the end of the addition of acetic anhydride; this addition was completed after 1 hour and 5 minutes. The mixture was allowed to sit with stirring at 0° C. for 18 hours and 15 minutes; after such time the mixture was a yellow slurry. A sample of the liquor was then taken for HPLC and NMR analysis. The mixture was then rinsed from the reactor with methyl-tert-butyl ether and filtered. The solid was washed with hexanes and allowed to air dry, which produced 108.17 g of off-white crystals. The crystals were analyzed by HPLC and found to be 99.82 percent (weight/weight) Meldrum's acid, melting point (m.p.) 88°–92° C. An additional 24.94 g of Meldrum's acid was determined to be in the liquor by HPLC analysis, for a total of 133.11 g (92.35 percent yield) of Meldrum's acid. Recrystallized Meldrum's acid from the methyl tert-butyl ether had a m.p. of 95°–96° C.

EXAMPLE 3

The procedures in Example 2 were substantially repeated except that 0.12 moles of sulfuric acid was used (instead of 0.06 moles as in Example 2). The total yield of Meldrum's acid was 82.96 mole percent.

We claim:

1. A process for preparing Meldrum's acid which comprises the steps of:
   (a) mixing acetone, malonic acid, and an acid catalyst in molar ratios from about 1.0:1.0:0.005 to about 2.3:1.0:0.12, respectively, to form a mixture comprising: a solution phase of the acetone, acid catalyst, and from about 5 to about 25 mole percent of the malonic acid; and a solid phase of from about 75 to about 95 mole percent of the malonic acid,
   (b) adding acetic anhydride to the mixture obtained from step (a), the total amount of acetic anhydride which is added is from about 0 percent molar excess to about 150 percent molar excess relative to the total malonic acid molar concentration, said addition of acetic anhydride occurring at a rate such that at any given time during the addition of acetic anhydride the concentration of unreacted acetic anhydride in the mixture does not exceed about 14 mole percent relative to the malonic acid molar concentration concurrently present in the solution phase.

2. The process of claim 1 wherein said acid catalyst is selected from the group consisting of hydrochloric acid, nitric acid, sulfuric acid, and aluminum trichloride.

3. The process of claim 1 wherein said acid catalyst is sulfuric acid.

4. The process of claim 1 wherein the concentration of unreacted acetic anhydride does not exceed about 0.1 mole percent during said addition of acetic anhydride, said percentage being based on the malonic acid molar concentration concurrently present in the solution phase.

5. The process of claim 1 wherein in step (a) the order of addition is acetone first, malonic acid second, and acid catalyst third.

6. The process of claim 1 carried out at a temperature between about −15° and 25° C.

7. The process of claim 1 carried out at a temperature of about 0° C.

8. The process of claim 1 wherein the molar ratio of acetone, malonic acid, and acid catalyst is about 1.14:1.0:0.06, respectively.

9. The process of claim 1 wherein the amount of acetic anhydride is about 25 percent molar excess, said percent molar excess being relative to the total malonic acid molar concentration.

10. The process of claim 1 wherein the reaction time for step (a) is not greater than about 8 hours.

11. The process of claim 1 wherein the reaction time for step (a) is not greater than about 2 hours.

12. The process of claim 1 wherein the reaction time for step (b) is less than about 3 days.

13. The process of claim 1 wherein the reaction time for step (b) is between about 15 hours and about 18 hours.

14. The process of claim 1 wherein the reaction mixture is purged with nitrogen.

15. The process of claim 1 wherein the concentration of unreacted acetic anhydride at any given time during the initial time of addition does not exceed about 0.1 mole percent, said percent based on the malonic acid molar concentration concurrently present in the solution phase.

* * * * *